United States Patent [19]

Cooper

[11] 4,039,535
[45] Aug. 2, 1977

[54] 7-[α-(GUANYL-1-UREIDO)-PHENYLACETAMIDO]-3-SUBSTITUTED CEPHALOSPORIN ANTIBIOTICS

[75] Inventor: Robin D. G. Cooper, Indianapolis, Ind.

[73] Assignee: Eli Lilly and Company, Indianapolis, Ind.

[21] Appl. No.: 663,885

[22] Filed: Mar. 4, 1976

Related U.S. Application Data

[63] Continuation of Ser. No. 423,027, Dec. 10, 1973, abandoned.

[51] Int. Cl.$^2$ .......................................... C07D 501/36
[52] U.S. Cl. ...................................... 544/26; 424/246
[58] Field of Search .................................. 260/243 C

[56] References Cited
U.S. PATENT DOCUMENTS

| 3,579,514 | 5/1971 | McGregor | 260/243 C |
|---|---|---|---|
| 3,734,907 | 5/1973 | Crast | 260/243 C |
| 3,757,015 | 9/1973 | Crast | 260/243 C |
| 3,766,175 | 10/1973 | Zemieux et al. | 260/243 C |
| 3,767,655 | 10/1973 | Cheney et al. | 260/243 C |
| 3,769,277 | 10/1973 | Long et al. | 260/243 C |
| 3,796,709 | 3/1974 | Breuer et al. | 260/243 C |
| 3,905,966 | 9/1975 | Kukolja et al. | 260/243 C |

*Primary Examiner*—Nicholas S. Rizzo
*Assistant Examiner*—David E. Wheeler
*Attorney, Agent, or Firm*—William B. Scanlon; Everet F. Smith

[57] ABSTRACT

7-[α-(guanyl-1-ureido)phenylacetamido]-3-(1-methyl-1H-tetrazol-5-ylthiomethyl)-3-cephem-4-carboxylic acid, 7-[α-(3-guanyl-1-ureido)phenylacetamido]-3-(5-methyl-1,3,4-thiadiazol-2-ylthiomethyl)-3-cephem-4-carboxylic acid and related compounds, the pharmaceutically acceptable non-toxic salts and certain esters thereof are valuable broad spectrum antibiotics demonstrating high levels of activity against Pseudomonas species.

7 Claims, No Drawings

7-[α-(GUANYL-1-UREIDO)PHENYLACETAMIDO]-3-SUBSTITUTED CEPHALOSPORIN ANTIBIOTICS

This is a continuation, of application Ser. No. 423,027, filed Dec. 10, 1973, now abandoned.

BACKGROUND OF THE INVENTION

The cephalosporin class of antibiotics has achieved an important role in the treatment and control of infectious diseases of man. For example, the well known cephalosporin antibiotics, cephalothin, cephaloglycin, cephaloridine and cephalexin have been widely accepted as valuable additions to the physicians armamentarium. Considerable effort continues to be extended in the development of new cephalosporin antibiotics with special antibiotic properties suited to the needs of the physician often times faced with particular infectious disease conditions.

DESCRIPTION OF THE PRIOR ART

Cephalosporin antibiotic compounds having a substitued α-amino group in the 7-arylacetamido side chain have been described. For example, U.S. Pat. No. 3,646,024 describes certain 7-[α-(3-imidoylureido)-arylacetamido]cephalosporanic acids. α-Ureido arylacetamidocephalosporanic acids are described in Ger. Offen. Nos. 2,055,337 and 2,127,178. U.S. Pat. No. 3,579,514 describes α-guanylureido substituted arylacetamido cephalosporanic acids wherein the aryl group is phenyl, substituted phenyl or thienyl and the substituent in the 3-position of the 3-cephem ring structure is methyl, acetoxymethyl, pyridinium methyl, picolinium methyl, or lutidinium methyl.

SUMMARY OF THE INVENTION

This invention relates to novel cephalosporin antibiotic compounds. In particular it relates to 7-[α-guanyl-1-ureido)phenylacetamido]cephalosporins and to certain phenyl substituted derivatives thereof which are substituted in the 3-position of the dihydrothiazine ring with a thiosubstituted tetrazole group of the formula $$-CH_2-S-\underset{\underset{R_1}{|}}{\overset{N \longrightarrow N}{\underset{N}{\bigvee}}}\overset{\|}{\underset{N}{\bigvee}}$$

or a 1,3,4-thia or oxadiazole group of the formula $$-CH_2-S-\overset{N \longrightarrow N}{\underset{Y}{\bigvee}}-R_2$$

wherein $R_1$ and $R_2$ are $C_1$–$C_4$ lower alkyl or phenyl and Y is O or S. The cephalosporin compounds of the invention exhibit a broad antibacterial spectrum and are especially active at low concentrations in inhibiting the growth of gram-negative organisms, in particular the pseudomonas such as *Pseudomonas aeroginosa*.

DETAILED DESCRIPTION

The cephalosporin antibiotic compounds of this invention are represented by the following structural formula $$\underset{H_2N-\underset{\underset{NH}{\|}}{C}-NH}{\overset{R'}{\underset{R}{\bigotimes}}}\overset{O=C}{\underset{NH}{|}}\overset{CH-\overset{O}{\overset{\|}{C}}-\overset{H}{\underset{}{N}}}{\overset{\|}{\underset{O}{\bigotimes}}}\overset{S}{\underset{N}{\bigotimes}}\overset{}{\underset{COOM}{CH_2-S-Z}}$$

wherein
R and R′ are independently hydrogen, hydroxy, methyl or chloro;
Z is selected from the group consisting of $$-\overset{N \longrightarrow N}{\underset{\underset{R_2}{|}}{\underset{N}{\bigvee}}}\overset{\|}{\underset{N}{\bigvee}} \qquad -\overset{N \longrightarrow N}{\underset{Y}{\bigvee}}-R_2$$

wherein
$R_1$ and $R_2$ are $C_1$–$C_4$ lower alkyl and
Y is O or S; and
M is hydrogen, a pharmaceutically acceptable cation or an acyloxymethyl group of the formula $$-CH_2-O-\overset{O}{\overset{\|}{C}}-R_3$$

wherein
$R_3$ is $C_1$–$C_4$ alkyl, phenyl or benzyl.

The above-defined cephalosporin compounds of the invention possess the novel structural feature of a thiadiazole, oxadiazole or 1H-tetrazole ring substituted on the 3-methylene group of the 3-cephem ring system via a connecting sulfur atom, coupled with an α-guanylureidophenylacetamido substituent as the side chain in the 7-position. The heterocyclic ring substituents are substituted, as shown, by phenyl or lower alkyl and preferably methyl, while the phenyl ring of the 7-position side chain can be substituted with methyl, chloro or an hydroxy group. These combined structural features contribute at least in part to the enhanced antibiotic activity demonstrated by the compounds of the invention in comparison with the previously known cephalosporin antibiotics having a somewhat similar structure.

Illustrative of the antibiotics described herein are the following named compounds:

7-[D-α-(3-guanyl-1-ureido)phenylacetamido]-3-(1-methyl-1H-tetrazol-5yl-thiomethyl)-3-cephem-4-carboxylic acid, 7-[D-α-(3-guanyl-1-ureido)-4-hydroxy-phenylacetamido]-3-(1-methyl-1H-tetrazol-5-ylthiomethyl)-3-cephem-4-carboxylic acids, 7-[D-α-(3-guanyl-1-ureido)-3-hydroxy-phenylacetamido]-3-(1-methyl-1H-tetrazol-5yl-thiomethyl)-3-cephem-4-carboxylic acid, 7-[D-α-(3-guanyl-1-ureido)phenylacetamido]-3-(5-methyl-1,3,4-thiadiazol-2yl-thiomethyl)-3-cephem-4-carboxylic acid, 7-[D-α-(3-guanyl-1-ureido)-3-hydroxy-phenylacetamido]-3-(5-methyl-1,3,4-thiadiazol-2yl-thiomethyl)-3-cephem-4-carboxylic acid, 7-[D-α-(3-guanyl-1-ureido)phenylacetamido]-3-(5-methyl-1,3,4-oxadiazol-2yl-thiomethyl)-3-cephem-4-carboxylic acid, 7-[D-α-(3-guanyl-1-ureido)phenylacetamido]-3-(5-ethyl-1,3,4-thiadiazol-2yl-thiomethyl)-3-cephem-4-carboxylic acid, 7-[D-α-(3-ureido)phenylacetamido]-3-(2-isopropyl-1H-tetrazol-5yl-thiomethyl)-3-cephem-4-carboxylic acid, 7-[D-α-(3-guanyl-1-ureido)-4-chloro-phenylacetamido]-3-(1-methyl-1H-tetrazol-5-ylthiomethyl)-3-cephem-4-carboxylic acid, 7-[D-α-(3-guanyl-1-ureido)-3-methyl-phenylacetamido]-3-(5-methyl-1,3,4-triadiazol-2-ylthiomethyl)-3-cephem-4-carboxylic acid, 7-[D-α-(3-guanyl-1-ureido)-4-chloro-phenylacetamido]-3-(5-methyl-1,3,4-oxadiazole-2-ylthiomethyl)-3-cephem-4-carboxylic acid, 7-[D-α-(3-guanyl-1-ureido)-2-chloro-phenylacetamido]-3-(1-methyl-1H-tetrazole-5-ylthiomethyl)-3-cephem-4-carboxylic acid, 7-[D-α-(3-guanyl-1-ureido)-3-chloro-4-hydroxy-phenylacetamido]-3-(1-methyl-1H-tetrazole-5-ylthiomethyl)-3-cephem-4-carboxylic acid, 7-[D-α-(3-guanyl-1-ureido)-3-methyl-4-hydroxy-phenylacetamido]-3-(5-methyl-1,3,4-triadiazole-2-ylthiomethyl)-3-cephem-4-carboxylic acid, 7-[D-α-(3-guanyl-1-ureido)-3,4-dichloro-phenylacetamido]-3-(1-methyl-1H-tetrazole-5-ylthiomethyl)-3-cephem-4-carboxylic acid, 7-[D-α-(3-guanyl-1-ureido)-4-hydroxy-phenylacetamido]-3-(5-phenyl-1,3,4-thiadiazol-2yl-thiomethyl)-3-cephem-4-carboxylic acid, and 7-[D-α-(3-guanyl-1-ureido)phenylacetamido]-3-(2-ethyl-1H-tetrazol-5yl-thiomethyl)-3-cephem-4-carboxylic acid.

The compounds of the invention form pharmaceutically acceptable, non-toxic salts with suitable inorganic and organic bases. For example, such salts as the alkali metal salts wherein M is a lithium, sodium or potassium cation and the alkaline earth metal salts, for example, when M is a divalent calcium ion, are prepared in a conventional manner by reacting the free acid form of the antibiotic, such as one of the above-named acids, with an alkali or alkaline earth metal base such as lithium carbonate, sodium bicarbonate, sodium carbonate, sodium hydroxide, potassium carbonate, potassium hydroxide, or calcium hydroxide. Salts of the antibiotics formed with organic bases are also suitable forms of the cephalosporins of this invention. Organic amines which can form salts include, for example, benzylamine, dibenzylamine, cyclohexylamine, dicyclohexylamine, diisopropylamine, the mono- and di-ethanolamines, hexamethylenetetramine, and ammonia. These cationic and amine salts can be used in the preparation of pharmaceutical formulations of the antibiotics suitable for parenteral administration.

The present invention further includes as one of its features the 7-[D-α-(3-guanyl-1-ureido)-substituted phenylacetamido]-3-(2-substituted 1H-tetrazole-5-ylthiomethyl or 5-substituted-1,3,4-oxa or thiadiazol-2-ylthiomethyl)-3-cephem-4-carboxylic acid acyloxymethyl esters, Formula I wherein M is acyloxymethyl. Examples of these esters are the $C_1$–$C_4$ lower alkanoyloxymethyl esters ($R_3$=$C_1$–$C_4$ lower alkyl) such as the acetoxymethyl, propionoxymethyl, and pivaloyloxymethyl esters and the esters wherein $R_3$ is phenyl or benzyl, namely the benzoyloxymethyl ester and the phenylacetoxymethyl ester.

The cephalosporin antibiotics of this invention are prepared by reacting a 7-D-phenylglycylamido-3-cephem-4-carboxylic acid having a 5-substituted-1,3,4-oxa- or thiadiazol-2-ylthiomethyl substituent or a 2-substituted-1H-tetrazol-5-ylthiomethyl substituent in the 3-position of the cephem ring structure with 4-guanylsemicarbazide and nitrous acid. The starting materials used in the preparation of the compounds of the invention, the 3-heterocyclic substituted 7-D-phenylglycylamidocephalosporins have been previously described and are readily prepared. 7-D-Phenylglycylamido-3-(2-methyl-1,3,4-thiadiazole-5-ylthiomethyl)-3-cephem-4-carboxylic acid and 7-D-phenylglycylamido-3-(5-methyl-1H-tetrazol-2yl-thiomethyl)-3-cephem-4-carboxylic acid, the hydroxy substituted derivatives and the phenyl and higher alkyl homologs thereof are described by C. W. Ryan in U.S. Pat. No. 3,641,021 issued Feb. 8, 1972. 7-D-Phenylglycylamido-3-(5-methyl-1,3,4-oxadiazol-2yl-thiomethyl)-3-cephem-4-carboxylic acid is described by L. B. Crast, Jr., in U.S. Pat. No. 3,734,907 issued May 22, 1973. These compounds can be prepared by the acylation of the desired 7-aminocephalosporin nucleus compound having the heterocyclic thiomethyl substituent in the 3-position of the 3-cephem ring system. The acylation is carried out with an active derivative of an amino-protected phenylglycine or substituted phenylglycine, for example with the acid chloride of N-t-butyloxycarbonylphenylglycine, by following well known acylation procedures. U.S. Pat. No. 3,641,021 describes a useful acylation method.

The preparation of the cephalosporin compounds of this invention is illustrated with 7-D-phenylglycylamido-3-(1-methyl-1H-tetrazol-5yl-thiomethyl)-3-cephem-4-carboxylic acid in the following generalized reaction scheme.

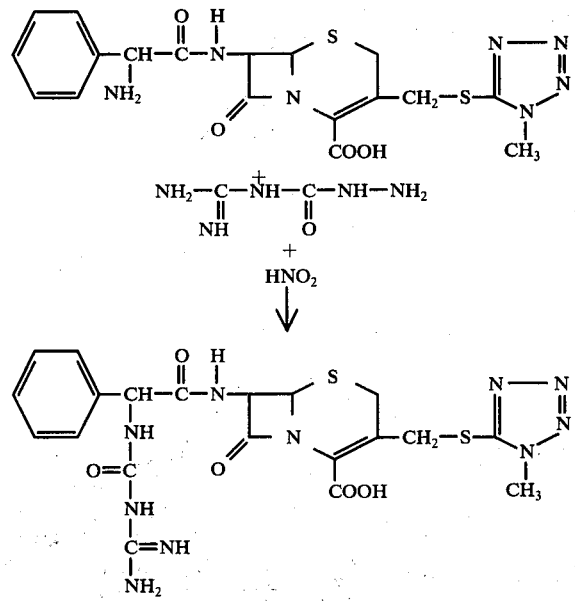

The reaction mechanism and the nature of the reaction intermediate formed with the guanylsemicarbazide is uncertain, however it appears to involve the in situ formation of a reactive species

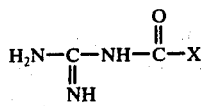

wherein X is a labile intermediate group formed with nitrous acid and the —NH—NH$_2$ group of the semicarbazide.

As previously mentioned the cephalosporin compounds of the invention possess a broad spectrum of antibiotic activity in that they inhibit the growth of both gram-positive and gram-negative microorganisms. In particular these compounds are highly active in inhibiting the growth of the gram-negative microorganisms of the genus pseudomonas. The compounds of the invention also possess a high order of activity against resistant staphylococcus and against strains of penicillinase producing staphylococcus.

The antibiotic activity of these cephalosporins is illustrated by the data presented in the following tables. In the tables the minimum inhibitory concentrations (MIC) of the listed compound verses the indicated gram-positive and gram-negative microorganisms is presented.

The MIC values were determined by the Gradient Plate Method which is essentially the method described by Bryson and Szybalski, *Science*, 116, 45–46 (1952).

Table I shows the in vitro antibiotic activity against representative G-microorganisms while Table II lists the activity (MIC values) against clinical isolates of penicillin resistant staphylococcus organisms both in the presence of and the absence of serum.

In the tables the test compounds are coded for convenience as follows:

1/A = 7-[D-α-(3-Guanyl-1-ureido)-phenylacetamido]-3-(1-methyl-1H-tetrazol-5yl-thiomethyl)-3-cephem-4-carboxylic acid.

B = 7-[D-α-(3-Guanyl-1-ureido)phenylacetamido]-3-(5-methyl-1,3,4-thiadiazol-2-yl-thiomethyl)-3-cephem-4-carboxylid acid.

C = 7-[D-α-(3-Guanyl-1-ureido)-4-hydroxyphenylacetamido]-3-(1-methyl-1H-tetrazol-5-yl-thiomethyl)-3-cephem-4-carboxylic acid.

D = 7-[D-α-(3-Guanyl-1-ureido)-4-hydroxyphenylacetamido]-3-(5-methyl-1,3,4-thiadiazol-2-yl-thiomethyl)-3-cephem-4-carboxylic acid E = 7-[D-α-(3-Guanyl-1-ureido)phenylacetamido]-3-acetoxymethyl-3-cephem-4-carboxylic acid.

TABLE I

ANTIBIOTIC ACTIVITY OF 7-[D-α-(3-GUANYL-1-UREIDO)-3-HETEROCYCLICTHIOMETHYL-3-CEPHEM-4-CARBOXYLIC ACIDS vs. GRAM—MICROORGANISMS

| Test Organism | Minimum Inhibitory Conc. (mcg/ml) Test Compound | | | | |
|---|---|---|---|---|---|
| | A | B | C | D | E |
| *Shigella sp.* | 2.0 | 5.5 | 0.7 | 4.5 | 16.3 |
| *Escherichia coli* | 2.0 | 8.7 | 0.7 | 6.0 | 13.8 |
| *Klebsiella pneumoniae* | 1.0 | 1.0 | 1.2 | 1.0 | 21.5 |
| *Aerobacter aerogenes* | 0.7 | 1.0 | 0.1 | 1.0 | 4.5 |
| *Salmonella heidelberg* | 0.8 | 6.0 | 0.2 | 1.0 | 6.0 |
| *Pseudomonas aeruginosa* | 53.5 | 104.0 | 23.0 | 50.0 | 100.0 |
| *Serratia marcescens* | 7.0 | 14.3 | 21.0 | 50.0 | 31.5 |

TABLE II

ANTIBIOTIC ACTIVITY OF 7-[D-α-(3-GUANYL-1-UREIDO)PHENYLACETAMIDO]-3-HETEROCYCLICTHIOMETHYL-3-CEPHEM-4-CARBOXYLIC ACIDS vs. PENICILLIN RESISTANT STAPHYLOCOCCUS

| Resistant Staph. | Minimum Inhibitory Concentration (mcg/ml) | | | | | | | | | |
|---|---|---|---|---|---|---|---|---|---|---|
| | A | | B | | C | | D | | E | |
| | N.S.[2] | S.[3] | N.S. | S | N.S. | S. | N.S. | S. | N.S. | S. |
| V41 | 0.7 | 1.0 | 1.0 | >20 | <0.1 | 10 | 1.0 | 6.0 | 0.5 | 1.0 |
| V32 | 1.0 | 9.0 | 1.0 | >20 | 1.0 | 10 | 1.0 | 12.0 | 0.7 | 1.0 |
| V84 | 0.6 | 1.0 | 0.6 | 10 | <0.1 | 1.0 | 1.0 | 2.0 | 0.6 | 1.0 |
| X1.1 | 0.5 | <0.1 | 0.6 | 10 | <0.1 | 0.6 | 1.0 | 1.0 | 0.6 | 1.0 |

[1]Test compounds A,B,C,D, and E are as named in Table I.
[2]N.S. = in the absence of serum.
[3]S = in the presence of serum.

In Tables I and II, the compound designated E is the known compound 7-[D-α-(3-guanyl-1-ureido)-phenylacetamido] cephalosporanic acid. This compound differs structurally from the compounds of this invention in that it possesses the acetoxymethyl group of the cephalosporanic acids in the 3-position of the dihydrothiazine ring of the 3-cephem ring system. As shown by the minimum inhibitory concentration values in Table I, the cephalosporin compounds of the present invention (as illustrated by test compounds A, B, C and D) possess significantly greater activity against gram-negative microorganisms than the known compound, E.

The cephalosporin compounds of this invention and the non-toxic, pharmaceutically acceptable salts thereof, such as the sodium and potassium salts, when administered parenterally, are useful in controlling infections in warm blooded mammals attributable to gram-negative and gram-positive microorganisms. The compounds of the invention can be formulated in pharmaceutical forms, such as in isotonic saline or as finely divided suspensions in injectable oils, for parenteral administration.

The acyloxymethyl esters of the cephalosporin antibiotics of this invention, Formula I, wherein M is an acyloxymethyl group of the formula

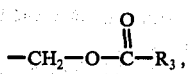

are useful forms of the antibiotics in that such esters provide for longer duration of the antibiotic activity of the parent acid. In addition, such esters are characterized as "active esters" since they possess antibiotic activity. This is in contrast to other cephalosporin esters which are, in general, either biologically inactive or mininally active.

The acyloxymethyl esters described herein are prepared by reacting an acyloxy halomethyl compound of the formula

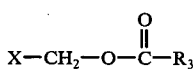

wherein X is chloro, bromo or iodo and $R_3$ is as defined above with an alkali metal or alkaline earth metal salt of a cephalosporin compound of the Formula I. The esterification is illustrated by the following reaction scheme.

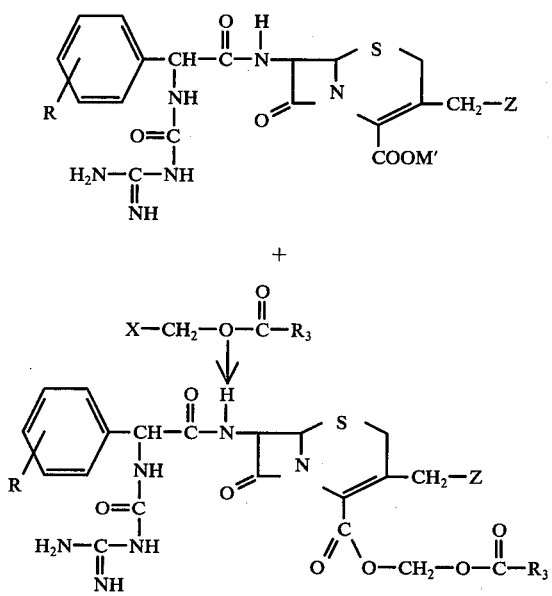

wherein M' is an alkali or alkaline earth metal cation and X and $R_3$ are as defined above. The esterification is carried out by reacting the salt of the cephalosporin with the halomethyl ester in an inert solvent, preferably an aqueous solvent at a temperature between 20° and 65° C. Inert solvents such as methylene chloride, acetone, water, dimethylformamide and tetrahydrofuran can be employed as well as mixtures thereof. Illustrative of the halomethyl acyloxy compounds represented by the formula

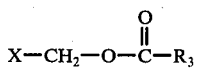

are bromomethyl acetate, bromomethyl propionate, chloromethyl pivalate, bromomethyl pivalate, chloromethyl benzoate, chloromethyl phenylacetate and bromomethyl phenylacetate.

Representative active esters are acetoxymethyl 7-[D-α-(3-guanyl-1-ureido)phenylacetamido]-3-(1-methyl-1H-tetrazol-5-5yl-thiomethyl)-3-cephem-4-carboxylate, pivaloyloxymethyl 7-[D-α-(3-guanyl-1-ureido)-phenylacetamido]-3-(5-methyl-1,3,4-thiadiazol-2yl-thiomethyl)-3-cephem-4-carboxylate and pivaloyloxymethyl 7-[D-α-(3-guanyl-1-ureido)phenylacetamido]-3-(2-methyl-1,3,4-thiadiazol-5yl-thiomethyl)-3-cephem-4-carboxylate and like esters.

A preferred group of cephalosporin antibiotics are represented by the following structural formula

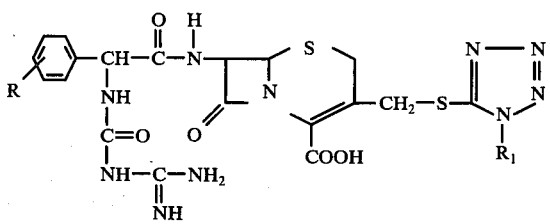

and the pharmaceutically acceptable salts and acyloxymethyl esters, thereof, wherein R is hydrogen or hydroxy and $R_1$ is $C_1$-$C_4$ lower alkyl or phenyl. Especially preferred compounds are represented when $R_1$ is methyl.

A further preferred group of antibiotics are represented by the formula

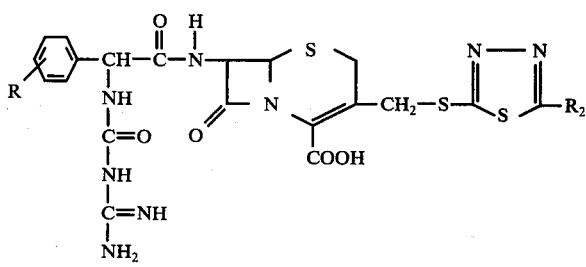

and the pharmaceutically acceptable salts and acyloxymethyl esters thereof, wherein R is hydrogen or hydroxy, and $R_2$ is $C_1$-$C_4$ lower alkyl or phenyl. A further preferred group of compounds are represented when $R_2$ in the above formula is methyl.

The above described antibiotic compounds, and their method of preparation are further illustrated by the following examples.

EXAMPLE 1

7-[D-α-(3-Guanyl-1-ureido)phenylacetamido]-3-(5-methyl-1,3,4-thiadiazol-2yl-thiomethyl)-3-cephem-4-carboxylic acid 7-(D-α-Phenylglycylamido)-3-(5-methyl-1,3,4-thiadiazol-2yl-thiomethyl)-3-cephem-4-carboxylic acid (477 mg) was suspended in 2 ml of water and solution was obtained by adjusting the pH of the suspension to pH 9.5 with triethylamine. To the solution was added a solution of 207 mg of 4-guanylsemicarbazide and 69 mg of sodium nitrite in 2 ml of water. The reaction mixture was stirred for one hour, was frozen in a dry ice bath and then stored for 15 hours in the refrigerator. The cold mixture which had thawed was filtered to collect the precipitate. The precipitate was washed with water and ether and was dried to afford 328 mg of amorphous product.

A 100 mg portion of the product was suspended in 1 ml of water and solubilized by adjusting the pH to 10 with triethylamine. The pH was then adjusted to pH 6.5 with phosphoric acid and the solution stirred for 1 hour in an ice bath. The product which had crystallized, was filtered, washed with water and dried under vacuum to yield 62 mg of dried crystalline product.

2

7-[D-α-(3-Guanyl-1-ureido)phenylacetamido]-3-(1-methyl-1H-tetrazole-5-yl-thiomethyl)-3-cephem-4-carboxylic acid To a cold suspension of 233 mg of 7-(D-α-phenylglycylamido)-3-(1-methyl-1H-tetrazol-5-yl-thiomethyl)-3-cephem-4-carboxylic acid in 2 ml of water triethylamine was added dropwise until a solution was obtained at about pH 9.5. A solution of 35 mg of sodium nitrite in 0.5 ml of water was cooled and mixed with a cold solution of 104 mg of guanylsemicarbazide in 1 ml of water and the cold mixed solution were added dropwise in stirring to the solution of the cephalosporin. The reaction was stirred for 2 hours in the cold and was then filtered. The filtered product was washed with water and ether and was dried. There was obtained 152 mg of 7-[D-α-(3-guanyl-1-ureido)phenylacetamido]-3-(1-methyl-1H-tetrazol-5yl-thiomethyl)-3-cephem-4-carboxylic acid.

EXAMPLE 3

Following the reaction procedures described in Example 2, 7-(D-4-hydroxyphenylglycylamido)-3-(1-methyl-1H-tetrazol-5ylthiomethyl)-3-cephem-4-carboxylic acid was reacted with a mixture of guanylsemicarbazide and sodium nitrite in aqueous solution and the insoluble reaction product is filtered, washed and dried to yield 7-[D-α-(3-guanyl-1-ureido)-4-hydroxyphenylacetamido]-3-(1-methyl-1H-tetrazol-5yl-thiomethyl)-3-cephem-4-carboxylic acid.

NMR (DMSOd$_6$) 3.55 (2H, broad singlet); 3.94 (3H, singlet), 4.37 (2H, broad singlet), 5.01 (1H, doublet, J=4.5Hz), 5.35 (1H, doublet, J=6Hz) collapsing to a singlet in D$_2$O), 5.87 (1H, quartet, J= 4.5Hz, 9Hz), 6.79 (2H, doublet J=8Hz), 7.19 (2H, doublet J=8Hz), 8.30 (5H, braod singlet, exchange with D$_2$O), 9.26 (1H, doublet J=9Hz exchanged with D$_2$O) and 9.4 (2H broad singlet, exchanges with D$_2$O) tau.

EXAMPLE 4

7-[D-α-(3-guanyl-1-ureido)-4-hydroxy-phenylacetamido]-3-(5-methyl-1,3,4-triadiazole-2yl-thiomethyl)-3-cephem-4-carboxylic acid was prepared with the corresponding D-phenylglycylamido-3-substituted cephalosporin and guanylsemicarbazide and sodium nitrite as carried out in the preceding examples.

NMR (DMSOd$_6$) 2.68 (3H, singlet) 6.46 (2H, quartet, J=13Hz), 5.1 (1H, doublet, J=5Hz), 5.33 (1H, multiplet) 5.90 (1H, quartet, J=5Hz, 10Hz), 6.68 (2H, doublet, J=8Hz), 7.19 (2H, doublet, J=8Hz), 7.9–8.9 (7H, broad), 9.25 (1H, doublet, J=10Hz).

I claim:
1. The compound of the formula

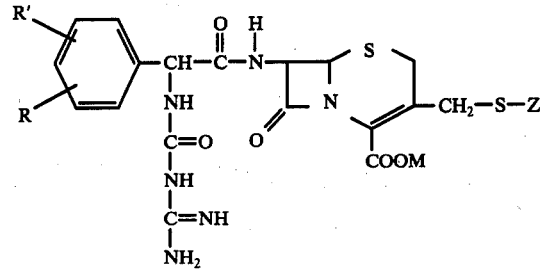

wherein
R and R' are independently hydrogen, hydroxy, methyl or chloro;
Z is selected from the group consisting of

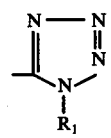 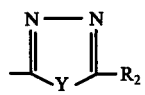

wherein
R$_1$ and R$_2$ are C$_1$–C$_4$ lower alkyl or phenyl, and
Y is O or S; and
M is hydrogen, a pharmaceutically acceptable cation or an acyloxymethyl group of the formula

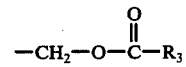

wherein
R$_3$ is C$_1$–C$_4$ alkyl, phenyl or benzyl.
2. The compound of claim 1 wherein Z is

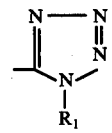

3. The compound of claim 2 wherein R$_1$ is methyl, and R and R' are hydrogen or hydroxy.
4. The compound of claim 3, said compound being 7-[D-α-(3-guanyl-1-ureido)phenylacetamido]-3-(1-methyl-1H-tetrazol-5-yl-thiomethyl)-3-cephem-4-carboxylic acid.
5. The compound of claim 1, wherein Z is

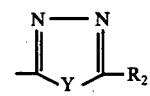

6. The compound of claim 5, wherein Y is S and R$_2$ is methyl.
7. The compound of claim 6, said compound being 7-[D-α-(3-guanyl-1-ureido)phenylacetamido]-3-(5-methyl-1,3,4-thiadiazol-2-yl-thiomethyl)-3-cephem-4-carboxylic acid.

* * * * *